United States Patent [19]
Voyce

[11] Patent Number: 5,263,492
[45] Date of Patent: Nov. 23, 1993

[54] RECORDING GONIOMETER

[76] Inventor: Guy Voyce, P.O. Box 999, Nyack, N.Y. 10960

[21] Appl. No.: 876,400

[22] Filed: Apr. 30, 1992

[51] Int. Cl.$^5$ .......................... A61B 5/103; G01B 9/10
[52] U.S. Cl. .................................... 128/782; 128/774; 33/471; 33/512
[58] Field of Search .................. 128/782, 774; 33/512, 33/515, 471, 1 N

[56] References Cited

U.S. PATENT DOCUMENTS

| | | | |
|---|---|---|---|
| 1,590,499 | 6/1926 | Cozad | 128/782 |
| 4,436,099 | 3/1984 | Raftopoulos | 128/782 |
| 4,485,825 | 12/1984 | Domján et al. | 128/782 |
| 4,549,555 | 10/1985 | Fraser et al. | 128/782 |
| 4,586,495 | 5/1986 | Petrofsky | 128/782 |
| 4,771,548 | 9/1988 | Donnery | 128/782 |
| 4,883,066 | 11/1989 | Widdoes et al. | 33/515 |
| 5,027,688 | 7/1991 | Suzuki et al. | 128/782 |

FOREIGN PATENT DOCUMENTS

| | | | |
|---|---|---|---|
| 596235 | 3/1978 | U.S.S.R. | 128/782 |
| 719635 | 3/1980 | U.S.S.R. | 128/782 |

*Primary Examiner*—Stephen C. Pellegrino
*Assistant Examiner*—Gary Jackson
*Attorney, Agent, or Firm*—Israel Nissenbaum

[57] ABSTRACT

A recording goniometer for affixation to an area surrounding a flexing joint. The goniometer measures and records the flexibility or extent of limb movement about a joint and further permits separate comparative recordation of joint movement as a determination of healing progress. The goniometer comprises extension elements distally connected to permit angular separation. For accuracy in measuring the extent of angular separation, the extension elements are also connected with a geared movement. In use, each extension element is removably attached to respective parts of the limb which extend from the joint, with the area of attachment proximally covering the joint. A platen member is integrated with one of the extension elements and a scribing element is inegrated with the other extension element. A replaceable recordation paper, with a preprinted measurement scale, is affixed to the platen member into writable contact with the scribing element, which circumscribes an arc on the recordation paper in congruence with the extent of movement of the joint. The scribing element is movable, along the radial length of the extension element with which it is integrated, into various locked positions. With such movement, it can record concentric arc segments which readily indicate comparative subtended arc segments as an indication of change or improvement of joint movement and the extent thereof.

9 Claims, 4 Drawing Sheets

RECORDING GONIOMETER

FIELD OF THE INVENTION

This invention relates to goniometers for measurement of joint movement during healing after an injury, and particularly to goniometers which record the extent of joint movement.

BACKGROUND OF THE INVENTION

Goniometers are instruments which measure the extent of movement of flexing joints such as the knee, ankle, wrist, shoulders, hips, fingers, etc. After injuries or illnesses which incapacitate a joint, recovery generally requires some form of physical therapy. Success in physical therapy treatment is measured by the extent to which the joint becomes more flexible over time. A modified protractor called a goniometer is placed against the joint and an angular reading of the extent of joint movement is taken as an indication of a patient's response to treatment. Readings are taken over preset intervals of time to plot the patient's progress. In U.S. Pat. No. 1,590,499, a very basic goniometer consisting of a protractor with a moving indicator is described which is strapped onto the limbs surrounding a joint. It has no recording capability and it permits only a direct one-time reading. In U.S. Pat. No. 4,306,571, a goniometer with three potentiometers is attached to a knee for recordation and dynamic joint motion analysis. The device however requires overly cumbersome a-nd expensive separate processing and recording instruments to analyze signals and to graphically record them. The connection to the processing and recording instruments also prevents utilization of the goniometer under real-life movement conditions.

Generally available present day commercial goniometers are usually simple instruments having two legs hinged together with an angular scale. A reading is taken and recorded and the instrument is stored. An example of such simple instrument is described in U.S. Pat. No. 4,771,548. This goniometer has a platform with a planar surface for a foot and a standard protractor-like scale for measurement of ankle flexibility. Newer, significantly more expensive goniometers electronically store joint motion readings of patients for downloading into computers. These goniometers are not however designed for active continuous motion and real life movement measurements but rather for single maximum readings.

SUMMARY OF THE INVENTION

It is an object of the present invention to provide a mechanical recording goniometer for either or both single time or continuous utilization, with wearing of the goniometer during activities.

It is a further object of the present invention to provide an economical device for providing hard copy instantly readable comparative measurements of joint flexibility.

These and other objects, features and advantages of the present invention will become more evident from the following discussion and the drawings in which:

DETAILED DESCRIPTION OF THE INVENTION

Figure 1:
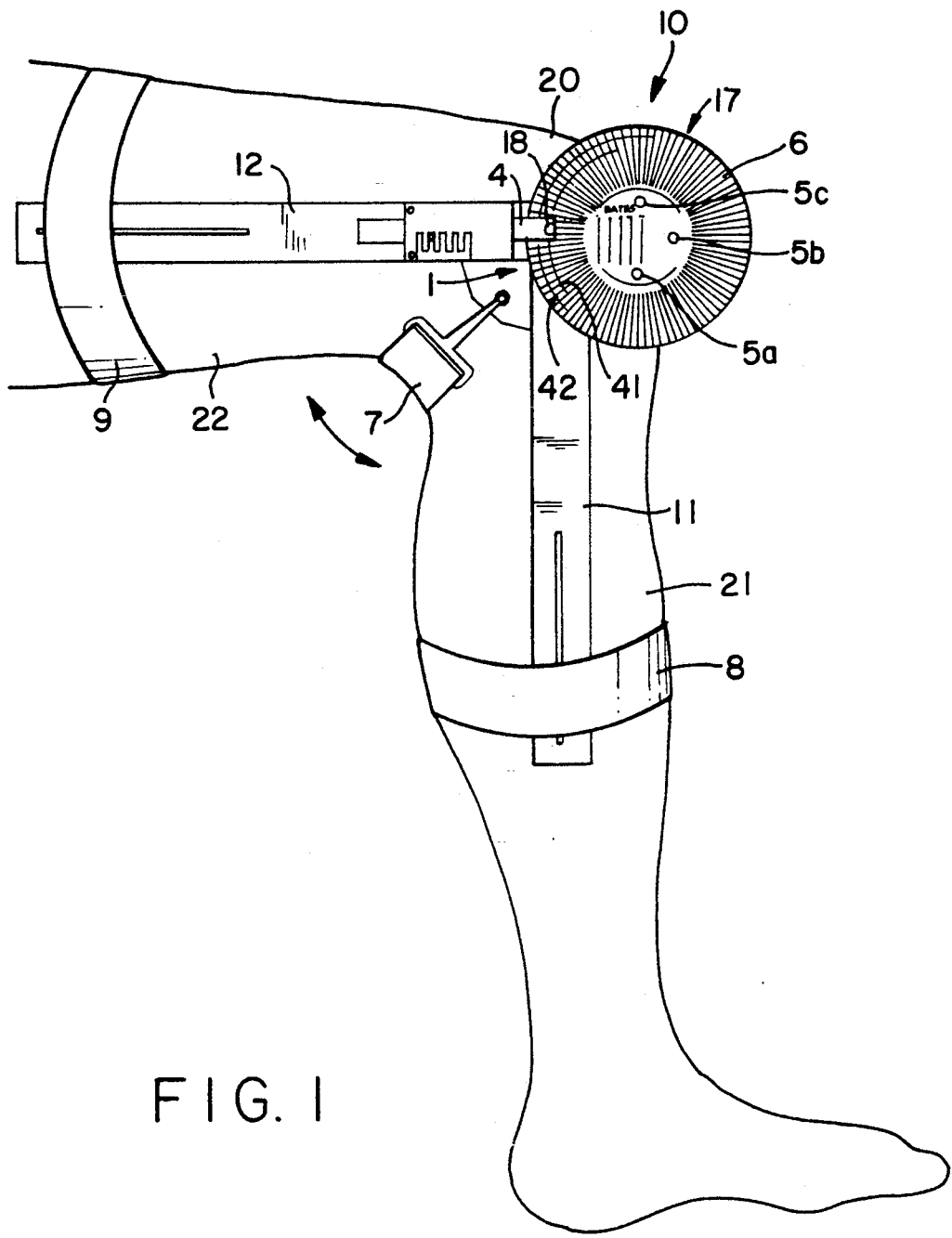
FIG. 1 is a view of the goniometer of the present invention shown attached to a knee for measurement of the extent of flexibility.

Generally the present invention comprises a recordation goniometer having a movable scribing element for permanent recordation of the extent of joint flexibility at various predetermined times during a healing process of the joint. The recordation goniometer comprises two elongated extension elements which are distally pivotally connected. The extension elements are adapted to be positioned co-extensive with members of a limb attached by a joint. The pivotal connection is in turn proximally positioned directly upon the joint. The extent to which the extension elements pivot away from each other, while positioned on the limb, constitutes a direct measurement of flexibility of the joint. For example, a pivoting to form an angle of about 170° between extension elements is indicative of normal knee flexibility. The scribing element is integrated with one of the extension elements whereby pivotal movement of the extension element causes a congruent movement of such scribing element with a recordation of an arc on recording medium with a preprinted measurement scale.

The recording medium, such as a removable paper disk, is supported on a platen member, integrated with the other extension member, with the paper disk overlapping or concentric with the joint on which the goniometer is placed. The scribing element, for example, a simple short pencil, preferably writes on the paper disk with a spring loaded pressure to ensure accuracy. The scribing element is radially movable for a distance along the longitudinal length of the extension element, to which it is integrated, which enables it to record on different concentric areas of the paper disk. Locking means secure the scribing element in various positions along the length of the extension element while remaining in contact with the supporting platen member. The scribing element is moved over pre-set or desired time intervals such that different arcs, corresponding to different times during the healing process, are juxtaposed for ready comparison showing the extent of healing or whether a treatment is efficacious or not. The variations in subtended arc segments indicate the extent of joint movement at the various time intervals. The paper disks are readily emplaced, removed and stored which enables the goniometer to be easily efficiently utilized with many patients.

Though less preferred, another type of recording medium is a material on the platen member which retains an impression and can be readily erased for successive use. In this embodiment, the scribing element comprises a stylus.

In order to further insure accuracy, it is preferred that the pivotally connected extension elements be connected via gear members rather than a simple pin pivot. This obviates possible slippage and inaccurate extent of recorded arcs. In addition, the geared pivotal connection readily permits, without loss of recording accuracy, the interchange and replacement of the extension elements more appropriate for the particular limbs and joints being observed. The combination of a circular disk and the geared pivotal connection (which permits full controlled circular movement of the extension members) allows the goniometer to be placed on either lateral side of a joint for appropriate measurement.

It is also preferred that the extension elements and if necessary, the pivoting portion as well, be provided with strap elements to hold the goniometer in place on the joint and limb. With such strap elements the goniometer can be readily worn for continued measurement of limb movement during actual use. Hook and eye fasteners, e.g. Velcro$^R$ permit rapid deployment and removal as well as providing a large holding range for use with patients of different dimensions.

DETAILED DESCRIPTION OF THE DRAWINGS AND THE PREFERRED EMBODIMENT

With specific reference to the drawings, in FIG. 1 goniometer 10 is shown for use in measurement of movement and flexibility of knee 20. Extensions 11 and 12 of goniometer 10 are attached to the leg 21 and thigh 22 respectively with adjustable straps 8 and 9 respectively. Pivot section 1, which is the connection of the distal ends of extensions 11 and 12, is placed on the knee 20 and is affixed thereto by adjustable strap 7. With affixation of the goniometer 10 to a limb, continuous, real life readings can be taken and recorded. Alternatively, the goniometer 10 can be merely placed against a limb such as knee 20 for a single instantaneous recorded measurement. Pivoting movement of the leg 21 and thigh 22 around the knee 20, as shown by the arrow, is mirrored by movement of the extensions 11 and 12. The movement is translated into arc 42 (more clearly seen in FIG. 4) on paper disk 6 by pencil 18 which is integrated with extension 12. Paper disk 6 is fitted on circular platen 17 (integrated with extension 11) and is removable therefrom for re-use. Arc 41 indicates a prior measurement and the difference in subtende arc between arcs 41 and 42 evidences the degree of improvement in flexibility of the knee 20.

Figure 2:
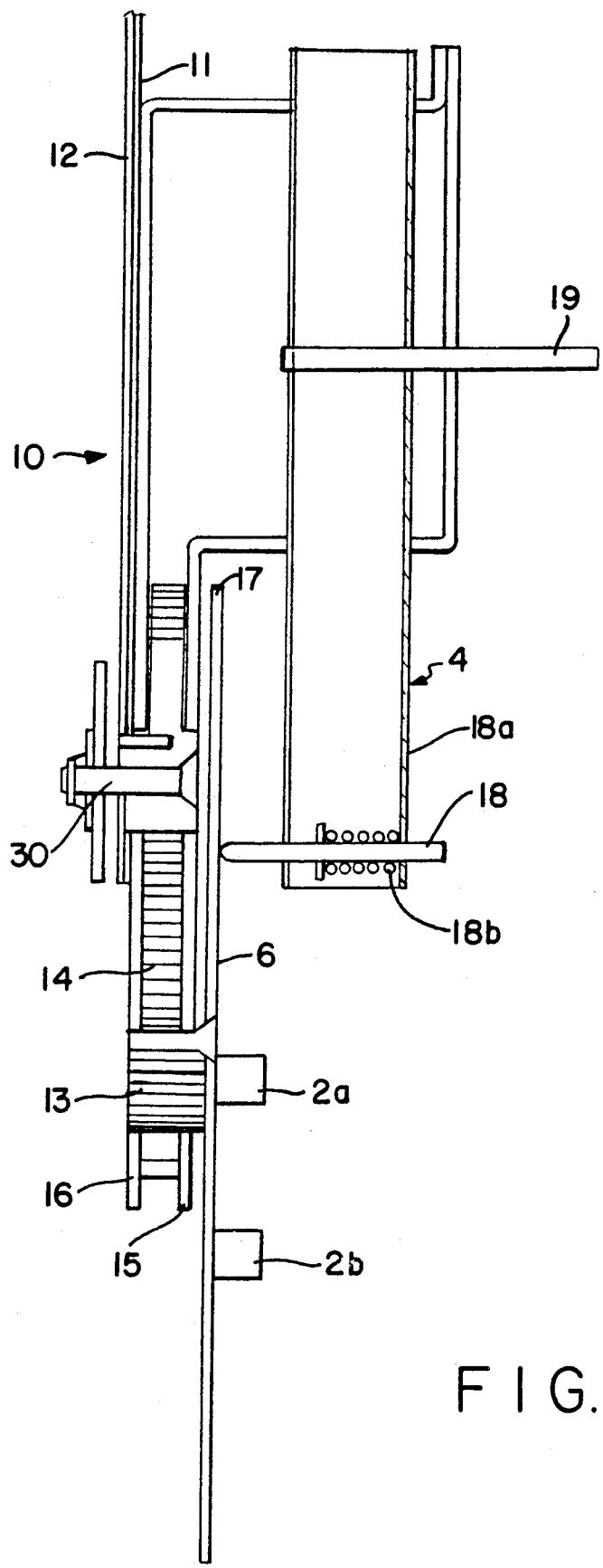
FIG. 2 is a side view of the goniometer of FIG. 1 showing the geared connection between the extension element as well as depicting the recording scribing element.
Figure 3:
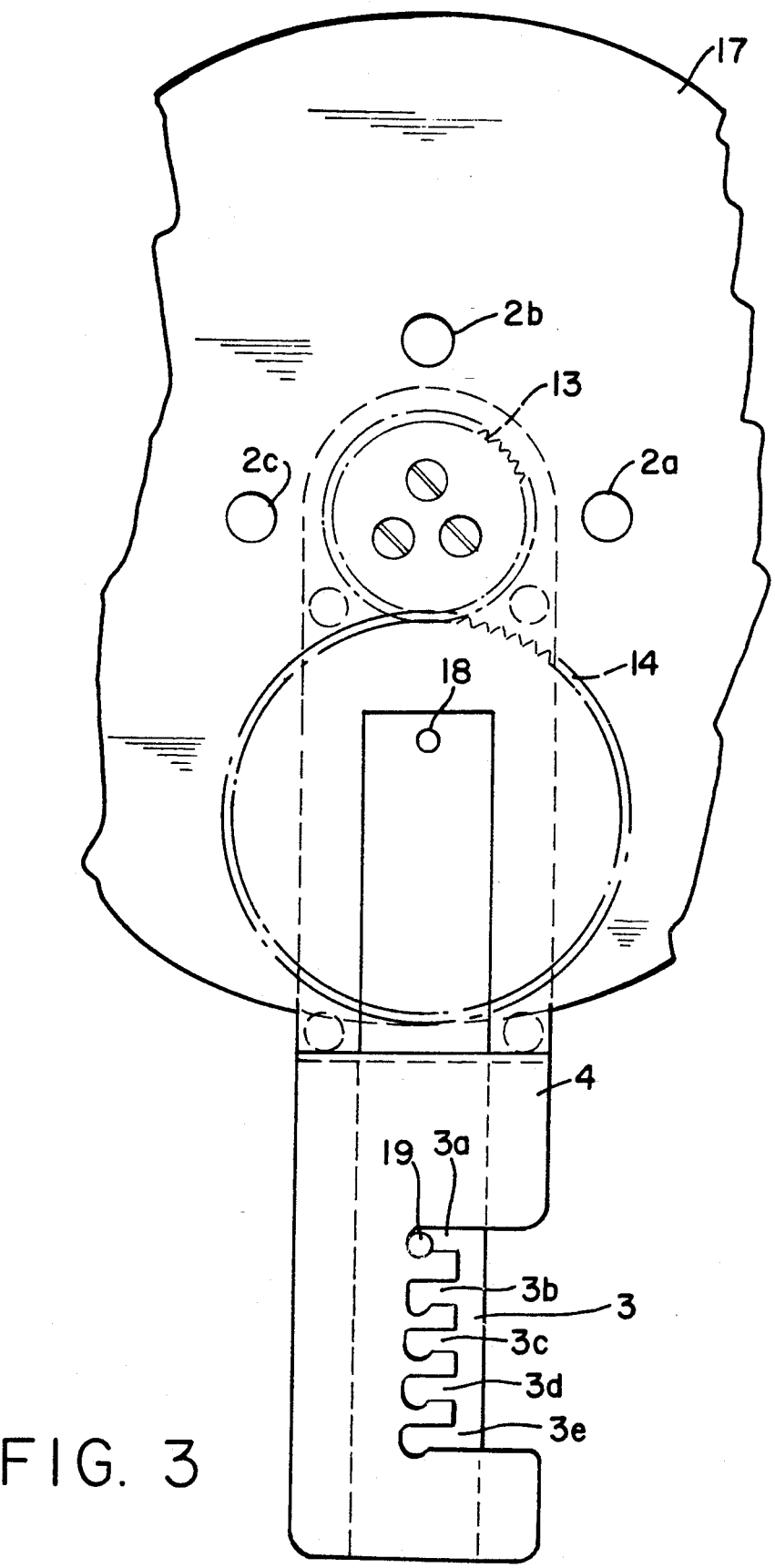
FIG. 3 is a partial top view of the goniometer of FIG. 2 with gears shown in phantom.
Figure 4:
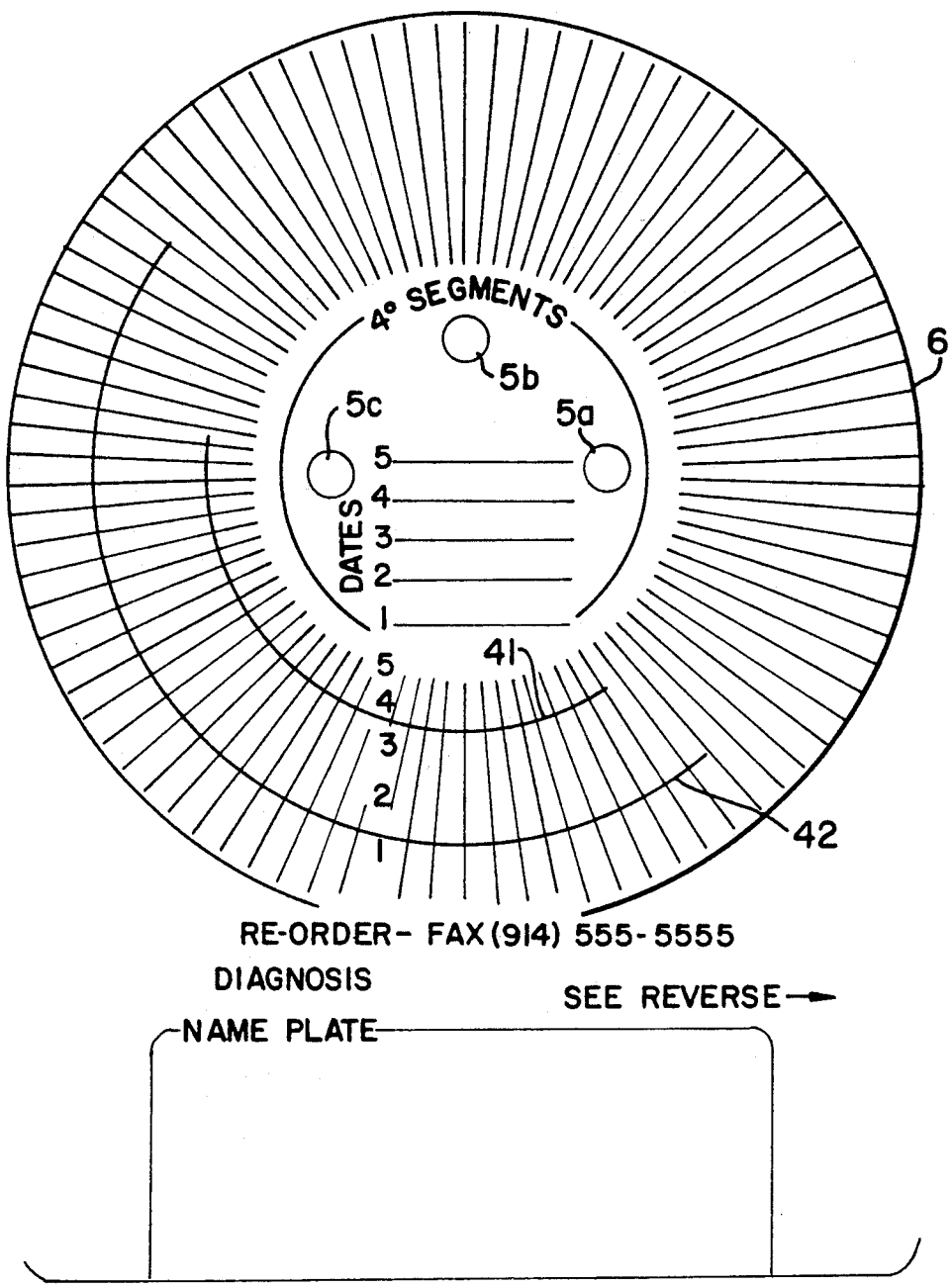
FIG. 4 is an example of a recordation paper showing successive flexibility measurements by the goniometer of the present invention.

FIGS. 2-4 more clearly illustrate the structure of the recording goniometer 10. Upper and lower frame members 15 and 16 terminate in extension members 11 and 12 respectively and confine gears 13 and 14, around which the extension members pivot. Extension members 11 and 12 are distally pivotally connected by pivot pin 30. Platen 17 is seated on upper frame member 15 with paper disk 6 placed on the platen. Protrusions 2a-c on platen 17 are sized and positioned to fit into apertures 5a-c in paper disk 6 whereby the paper disk is properly positioned and prevented from slipping during recordation. Support structure 4 for pencil 18 is affixed to lower frame member 16 and is U-shaped to permit pencil 18 to be in overlapping perpendicular position relative to platen 17 and paper disk 6. Pencil 18 and control lever 19 are perpendicular to and held by tube 18a which is in turn movable through the U of support structure 4. Support structure 4, as more clearly seen in FIG. 3, comprises slotted track 3 with lateral locking slots 3a-e. Control lever 19 located within slotted track 3 is movable therein and into locking positions 3a-e, as desired. Movement of the control lever 19 causes pencil 18 to move radially relative to paper disk 6 whereby it can record different arc segments on the paper disk. Pencil 18 is biased against the paper disk 6 by spring 18b whereby relative movement between extension members 11 and 12 causes the pencil to record arcs 41 and 42 shown in FIG. 4. The goniometer 10, as shown will permit the separate recordation of five separate arcs for comparative purposes over any predetermined periods of time. It is understood however that different numbers of locking positions for the pencil 18 to assume are possible.

It is understood that the above described and illustrated goniometer is merely illustrative of the present invention and that changes in structure and operation may be made without departing from the scope of the present invention as defined in the following claims.

What is claimed is:

1. A goniometer for measurement of the flexibility and extent of limb movement about a joint, said goniometer comprising two elongated extension elements distally pivotally connected, characterized in that a platen member is integrated with one of the extension elements and a scribing element is integrated with the other extension element, with said platen member providing a support for a recordation element whereby, when said extension elements are affixed to limb portions on opposite sides of a joint and the pivotal connection is proximally placed on the joint, the scribing element circumscribes and records an arc, on the recordation element, in congruence with the extent of movement of the joint.

2. The goniometer of claim 1 wherein the extension element, with which the scribing element is integrated, comprises means for permitting said scribing element to be movable, along the length of the extension element with which it is integrated, and means for locking said scribing element into one of at least two positions along said radial length.

3. The goniometer of claim 2 wherein said recording element comprises a removable paper disk with a preprinted scale.

4. The goniometer of claim 1 wherein said pivotal connection comprises at least two intermeshed gears.

5. The goniometer of claim 1 wherein said scribing element is spring biased against said recording element.

6. A goniometer for measurement of the flexibility and extend of limb movement about a joint, said goniometer comprising two elongated extension elements distally pivotally connected, characterized in that a platen member is integrated with one of the extension elements and a scribing element is integrated with the other extension element, with said platen member providing a support for a recordation element whereby, wherein said extension elements are affixed to limb portions on opposite sides of a joint and the pivotal connection is proximally placed on the joint, the scribing element circumscribes and records an arc, on the recordation element, in congruence with the extent of movement of the joint, wherein the extension element, with which the scribing element is integrated, comprises means for permitting said scribing element to be movable, along the length of the extension element with which it is integrated, and means for locking said scribing element into one of at least two positions along said radial length, wherein said pivotal connection comprises at least two intermeshed gears, and wherein said goniometer comprises two frame elements which sandwich said intermeshed gears therebetween with said extension elements being affixed respectively to said frame elements.

7. The goniometer of claim 6 wherein the extension elements comprises means for removal thereon from the goniometer, whereby extension elements suitable for use with different limbs and joints may be utilized.

8. A goniometer for measurement of the flexibility and extent of limb movement about a joint, said goniometer comprising two elongated extension elements distally pivotally connected, characterized in that a platen member is integrated with one of the extension elements and a scribing element is integrated with the other extension element, with said platen member providing a support for a recordation element whereby, when said extension elements are affixed to limb portions on opposite sides of a joint and the pivotal connection is proximally placed on the joint, the scribing element circumscribes and records an arc, on the recordation element, in congruence with the extent of movement of the joint, wherein the extension element, with which the scribing element is integrated, comprises means for permitting said scribing element to be movable, along the length of the extension element with which it is integrated, and means for locking said scribing element into one of at least two positions along said radial length, wherein said recording element comprises a removable paper disk with a preprinted scale, wherein said scribing element is perpendicularly affixed to a support member and wherein a lever member is perpendicularly affixed to the support member at a point distant from the scribing element, whereby movement of said lever member causes corresponding movement of said scribing element and wherein said means for permitting movement of the scribing element comprises a slotted track longitudinally positioned relative to the extension element to which the scribing element is affixed, with said lever being movably positioned within said track.

9. The goniometer of claim 8 wherein said means for locking said scribing element into at least two positions comprises lateral slots leading from said track and into which said lever member is movable.

* * * * *